United States Patent [19]

Mott

[11] Patent Number: 5,041,657

[45] Date of Patent: Aug. 20, 1991

[54] PREPARATION OF AROMATIC ACETAMIDES FROM ARYL METHYL KETONES

[75] Inventor: Graham N. Mott, Corpus Christi, Tex.

[73] Assignee: Hoechst Celanese Corporation, Somerville, N.J.

[21] Appl. No.: 555,277

[22] Filed: Jul. 19, 1990

[51] Int. Cl.$^5$ ............................................ C07C 231/10
[52] U.S. Cl. .................................. 564/145; 564/176; 564/177
[58] Field of Search ................ 564/145, 176, 177, 145

[56] References Cited

U.S. PATENT DOCUMENTS

| | | | |
|---|---|---|---|
| 2,459,706 | 1/1949 | King | 260/561 |
| 2,572,809 | 10/1951 | Jelinek | 260/247.1 |
| 2,610,980 | 9/1952 | Naylor | 260/558 |
| 2,689,246 | 9/1954 | Feichtinger | 260/247.1 |

FOREIGN PATENT DOCUMENTS 747961 12/1966 Canada .
405675 11/1924 Fed. Rep. of Germany .

OTHER PUBLICATIONS

*Synthesis* 1975, Jun. 1975, 358–375.
R. Adam, Ed., *Organic Reactions*, vol. III (New York: John Wiley, 1946), 83–107.
*J. Amer. Chem. Soc.* 68 (1946), 2633–2634.

*Primary Examiner*—Glennon H. Hollrah
*Assistant Examiner*—Shailendra Kumar
*Attorney, Agent, or Firm*—Shirley L. Church; Marvin Turken

[57] ABSTRACT

A method is provided for preparing aromatic acetamides comprising reacting an aryl methyl ketone containing the same number of carbon atoms as the aromatic acetamide, with sulfur and ammonia under substantially anhydrous conditions. The method is particularly useful for the preparation of 4-hydroxyphenylacetamide from 4-hydroxyacetophenone.

9 Claims, No Drawings

PREPARATION OF AROMATIC ACETAMIDES FROM ARYL METHYL KETONES

BACKGROUND OF THE INVENTION

1. Field Of The Invention

This invention relates to a new method of preparing aromatic acetamides from aryl methyl ketones.

2. Background Information And Description Of The Related Art

The following information is disclosed in accordance with the terms of 37 CFR 1.56, 1.97 and 1.98.

Aromatic acetamides are useful as intermediates in the production of various chemicals and pharmaceuticals. For example, 4-hydroxyphenylacetamide is an intermediate in the production of atenolol, a well-known beta-adrenergic blocker.

The Willgerodt reaction is known in the art as the reaction between an aryl alkyl ketone and aqueous yellow ammonium polysulfide to produce an aromatic amide having the same number of carbon atoms. For example, by means of this reaction, 4-hydroxyphenylacetamide may be produced from 4-hydroxyacetophenone.

In addition to aryl alkylketones, the reaction has been stated to be applicable to the production of amides from other compounds, such as dialkyl ketones, aliphatic mercaptans, secondary and tertiary alcohols, acetals, and aromatic hydrocarbons. It has also been stated that a mixture of sulfur and ammonia is equivalent to ammonium polysulfide in obtaining the reaction.

In the Kindler modification of the Willgerodt reaction, the aryl alkyl ketone or other reactant is reacted with an amine and sulfur in an anhydrous system. However, as described in the art, the product in this modification is not the amide but the thioamide.

Description of the foregoing reactions are exemplified in the following references.

U.S. Pat. No. 2,459,706 issued Jan. 18, 1949 to J. A. King, discloses the production of amides by subjecting aliphatic mercaptans or secondary or tertiary alcohols to a Willgerodt reaction with ammonium polysulfide, or sulfur and ammonia or an amine. In column 3, lines 5 to 7, the patentee states that "When substantially anhydrous conditions prevail, the carboxylic derivative resulting is a thioamide . . . ."

U.S. Pat. No. 2,572,809 issued Oct. 23, 1951 to C. F. Jelinek, discloses the Willgerodt reaction between acetals and ammonium polysulfide, or ammonium hydroxide and sulfur in an aqueous system, or a primary or secondary amine and sulfur in an anhydrous system, to produce amides. Example 5 in column 3 of the patent shows the reaction between dimethyl benzal, sulfur and morpholine to produce a thioamide, viz., 4-thiobenzoyl-morpholide.

U.S. Pat. No. 2,610,980 issued Sept. 16, 1952 to M. A. Naylor, teaches the formation of amides by reacting aromatic hydrocarbons with ammonium polysulfide, or sulfur and ammonia in the presence of water or under anhydrous conditions. In column 5, lines 35 to 37, the patentee states, "When substantially anhydrous conditions prevail, the carboxylic acid derivative resulting is a thioamide."

U.S. Pat. No. 2,689,246 issued Sept. 14, 1954 to H. Feichtinger, discloses the Willgerodt reaction of unsaturated nitrocompounds with ammonium polysulfide, or ammonia or an amine and sulfur, in aqueous system to form a carboxylic acid amine, or in anhydrous system to form a corresponding thioamide.

German Patent No. 405,675, granted Nov. 4, 1924 to K. Kindler, discloses generally the preparation of thioamides by reacting aldehydes or ketones with ammonia or a primary or secondary amine, and sulfur. However, in the only specific example utilizing ammonia gas, benzaldehyde is reacted to form thiobenzamide.

E. V. Brown, "The Willgerodt Reaction" in *Synthesis* 1975, June 1975, 358–375, discloses the Willgerodt reaction of various aryl methyl ketones and other compounds with ammonium polysulfide, or sulfur and ammonium hydroxide in aqueous system to produce aryl acetamides, or with sulfur and an amine such as morpholine in a Willgerodt-Kindler reaction to produce thioamides.

M. Carmack and M. A. Spielman, "The Willgerodt Reaction", Chapter 2 of R. Adams, Editor, *Organic Reactions*, Vol. III, (New York: John Wiley, 1946), 83–107, disclose the Willgerodt reaction of several methyl aryl ketones with ammonium polysulfide, or sulfur and aqueous ammonia to produce aromatic acetamides, and also show examples of the Kindler modification involving the reaction of any of various methyl aryl ketones with sulfur and amines in anhydrous system to produce acetothioamides. This reference also states that anhydrous ammonia sometimes is used (page 85), citing German Patent No. 405,675 described previously.

A. C. Ott, et. al., *J. Amer. Chem. Soc.* 68 (1946): 2633–2634, discloses the preparation of p-hydroxyphenylacetamide by the Willgerodt reaction of p-hydroxyacetophenone and ammonium sulfide in aqueous system.

SUMMARY OF THE INVENTION

In accordance with this invention, a method is provided for preparing aromatic acetamides comprising reacting an aryl methyl ketone containing the same number of carbon atoms as the aromatic acetamide, with sulfur and ammonia under substantially anhydrous conditions. It has been found, surprisingly, that the aromatic acetamide rather than the corresponding acetothioamide is produced despite the substantially universal teaching in the literature that only the thioamide is produced under anhydrous conditions.

A significant advantage of the process of the invention is that, since the process is carried out under substantially anhydrous conditions, it provides for the production of aromatic acetamides without the necessity of having to separate the product from the appreciable amounts of water which are present when other, previously known, synthesis techniques are used.

DESCRIPTION OF PREFERRED EMBODIMENTS

The process of this invention is based on the following reaction:

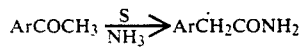

where Ar is an aryl group. Ar may be, for example, phenyl, 1-naphthyl, 2-naphthyl, 4-biphenyl, 2-phenanthryl, 1-pyrenyl, or 2-benzyloxyphenyl, with the foregoing aryl groups being unsubstituted or having at least one ring hydrogen atom substituted with hydroxy; alkyl or alkoxy having 1 to 5 carbon atoms; halide, including chloride, bromide, iodide and fluoride; amino with the amino nitrogen bonded to hydrogen or alkyl containing up to 5 carbon atoms; or acetamido. In general, it is preferred that not more than two ring hydrogen atoms of any of the foregoing aryl groups be substituted with any of the foregoing substituents. Phenyl is the preferred aryl group and the most preferred aryl methyl ketone is 4-hydroxyacetophenone which is reacted in accordance with the method of this invention to form 4-hydroxyphenylacetamide.

In carrying out the method of this invention, sulfur may be initially present in an amount, for example, of about 1 to 10, preferably about 1.5 to 5 moles per mole of ketone initially added, and anhydrous ammonia may be initially present, for example in an amount of about 1 to 20, preferably about 5 to 10 moles per mole of ketone.

Although the reaction may be carried out in the absence of solvent, it is advantageous in many instances to have an inert solvent present. The choice of solvent will depend largely on the solubilities of the ketone reactant and the aromatic acetamide product in the solvent. Depending on such solubilities, the solvent may be, for example, an alkanol containing 1 to 10 carbon atoms, dioxane, quinoline, pyridine, a glycol, or combinations thereof. The solvent when used is generally present in an amount such that a solution of about 5 to 50, preferably about 10 to 25 wt% of ketone based on the weight of the solution, is initially obtained.

The reaction is carried out at a temperature high enough to obtain a satisfactory rate of reaction but not high enough to cause significant decomposition of the ketone reactant and/or product, and a pressure high enough to keep a sufficient amount of ammonia dissolved in the liquid reaction but not substantially higher than is necessary for this purpose, for a reaction time sufficient to obtain a satisfactory yield of desired product. In many instances, the reaction temperature will be in the range of about 100° to 200° C. and a pressure of about 0 to 1000 psig, for a reaction time of about 0.5 to 6 hours.

When 4-hydroxyacetophenone is being reacted to form 4-hydroxyphenylacetamide, the solvent is preferably isopropanol, generally used in an amount to yield an initial solution of about 10 to 25 wt % of 4-hydroxyacetophenone based on the weight of the solution, and the reaction is preferably carried out at a temperature of about 140° to 180° C. and a pressure of about 200 to 600 psig, for a reaction time of about 1 to 4 hours.

The inventive method may be further illustrated by the following example.

EXAMPLE

4-Hydroxyacetophenone in an amount of 16.7 g (0.12 moles), sulfur in an amount of 10.2 g (0.32 moles), and isopropanol in an amount of 58 g were charged to a 300 ml Hastelloy C autoclave. The autoclave was sealed, evacuated, and cooled and anhydrous ammonia in an amount of 12 g (0.71 moles) was introduced. The reaction mixture was heated to 160° C. and vigorously stirred for 2 hours during which time the autogenous pressure in the autoclave rose from 215 psig. at the beginning of the reaction to 235 psig. at the end of the reaction. The mixture was then cooled and evaporated. Recrystallization of the residue from water and then acetic acid/toluene afforded a 65% yield of 4-hydroxyphenylacetamide.

What is claimed is:

1. A method for preparing aromatic acetamides, comprising:

reacting an aryl methyl ketone containing the same number of carbon atoms as the aromatic acetamide, with sulfur and ammonia under substantially anhydrous conditions at a temperature ranging from about 100° C. to about 200° C. and a pressure ranging from about 0 psig to about 1,000 psig, and wherein said aryl is selected from the group consisting of phenyl, 1-naphthyl, 2-naphthyl, 4-biphenyl, 2-phenanthryl, 1-pyrenyl, and 2-benzyloxyphenyl, and wherein said aryl group is unsubstituted or has at least one ring hydrogen atom substituted with hydroxy; alkyl or alkoxy having 1 to 5 carbon atoms; halide, including chloride, bromide, iodide and fluoride; amino with the amino nitrogen bonded to hydrogen or alkyl containing up to 5 carbon atoms; acetamido; or combinations thereof.

2. The method of claim 1 wherein the sulfur is initially present in an amount of about 1 to 10 moles per mole of said ketone and the ammonia is initially present in an amount of about 1 to 20 moles per mole of said ketone.

3. The method of claim 2 carried out in the presence of an inert solvent.

4. The method of claim 3 wherein said solvent is present in an amount such that a solution of about 5 to 50 wt % of ketone is initially obtained based on the weight of the solution.

5. The method of claim 4 carried out for a reaction time of about 0.5 to about 6 hours.

6. The method of claim 2 wherein said aromatic acetamide is 4-hydroxyphenylacetamide and said ketone is 4-hydroxyacetophenone.

7. The method of claim 6 carried out in the presence of isopropanol as an inert solvent.

8. The method of claim 7 wherein said isopropanol is present in an amount such that a solution of about 10 to 25 wt % of 4-hydroxyacetophenone is initially obtained, based on the weight of the solution.

9. The method of claim 8 carried out at a temperature of about 140° to 180° C. and a pressure of about 200 to 600 psig, for a reaction time of about 1 to 4 hours.

* * * * *